US00PP14035P39

(12) United States Plant Patent
Hall

(10) Patent No.: US PP14,035 P3
(45) Date of Patent: Jul. 29, 2003

(54) RASPBERRY VARIETY NAMED 'MOTUEKA'

(75) Inventor: Harvey K Hall, Motueka (NZ)

(73) Assignee: The Horticulture and Food Research Institute of New Zealand Limited, Palmerston North (NL)

( * ) Notice: Subject to any disclaimer, the term of this patent is extended or adjusted under 35 U.S.C. 154(b) by 243 days.

(21) Appl. No.: 09/866,445

(22) Filed: May 25, 2001

(65) Prior Publication Data

US 2002/0194655 P1 Dec. 19, 2002

(51) Int. Cl.[7] ..... A01H 5/00

(52) U.S. Cl. ..... Plt./204

(58) Field of Search ..... Plt./204

(56) References Cited

PUBLICATIONS

UPOV–ROM GTITM Computer Database, 2001/06, GTI Jouve Retrieval Software, citation for 'Motueka'.*

* cited by examiner

*Primary Examiner*—Bruce R. Campell
*Assistant Examiner*—Susan B. McCormick
(74) *Attorney, Agent, or Firm*—Greenlee, Winner and Sullivan, P.C.

(57) ABSTRACT

A new and distinct floricane fruiting variety of red raspberry, named 'Motueka', botanically identified as *Rubus idaeus* L. is described. The new variety is distinguished from others by its high yields of medium sized, high flavored, moderately bright and medium red berries. The plant exhibits a spine-free upright growth habit of medium vigor. The fruit are suitable for consumption as fresh berries and are also amenable to processing. Fruit are detached easily and the variety is well suited for harvest by machine as demonstrated in trials with a Korvan 9000 harvester. In addition, the plant has displayed resistance to Raspberry Bushy Dwarf Virus (RBDV).

4 Drawing Sheets

Genus and species of plant claimed: *Rubus idaeus.*

BACKGROUND OF THE INVENTION

The new variety of red raspberry, *Rubus idaeus* L, was created in the course of a planned breeding program carried out at HortResearch Nelson, New Zealand. The parents used to make the cross in 1989 were the selections B257 (seed parent) and F29 (pollen parent). B257 was selected from open pollinated seed of the Scottish Crop Research Institute selection 7936F5 grown at HortResearch Nelson. F29 was selected from the cross 'Marcy'×'Malling Delight' produced on behalf of HortResearch at the Canada Agriculture Station at Abbotsford, British Columbia and grown at HortResearch Nelson.

The parentage of the new variety also includes the Scottish varieties 'Glen Prosen' (not patented) and 'Glen Clova' (not patented), the German variety 'Rumiloba' (not patented) and the United States variety 'Carnival' (not patented). The background of 'Motueka' also includes *Rubus occidentalis* via the Scottish breeding program and spinelessness from the old Scottish variety 'Burnetholm'.

Seedlings were grown in the field at HortResearch Nelson and the original plant of the new variety was selected during the 1992–93 summer (Southern Hemisphere) and was found to exhibit:

(a) a spine-free upright growth habit of medium vigor, (b) the ability to form attractive, medium sized mid red fruit of good flavor in exceptionally high yields on medium length fruiting laterals, (c) resistance to Raspberry Bushy Dwarf Virus (RBDV), and (d) adaptation for machine harvest.

The new variety was first asexually propagated in 1993, reproduced by vegetative cuttings arising from root cuttings. Cuttings developed in spring in this way root within a 3–4 week propagation period, plants suitable for field planting are then generally ready in autumn of the same year. The resulting plants propagated true to type demonstrating that the characteristics of the new variety are stable and are transmitted without change through succeeding generations.

SUMMARY OF THE INVENTION

The new variety was tested and evaluated during the period 1995 to 2000 at HortResearch Nelson.

When compared to the parent B257, the new variety is found to form larger, almost as firm fruit, in higher yields. 'Motueka' is further distinguished from B257 by having fruit that are thicker, longer, more conical, with darker color, increased shininess, and reduced force required to separate the berry from the plug.

When compared to the F29 parent the new variety exhibits larger, coherent, non crumbly, medium red fruit in higher yields, a similar picking date (i.e. mid season), and a longer picking period. 'Motueka' is further distinguished from F29, by having no spines on juvenile or mature canes, by reduced cane vigor and cane number, and by having larger fruit that are very easy to separate from the plug.

Data collected during the evaluation period comparing fruiting performance of the new variety with standard New Zealand varieties is presented in Table 1.

TABLE 1

Comparison of fruiting performance.

| Variety | Average Yield (T/ha) | Berry Weight (g) |
|---|---|---|
| 'Motueka' | 28.6 | 3.5 |
| 'Marcy' | 21.1 | 2.8 |
| 'Skeena' | 15.8 | 3.3 |
| 'Chilliwack' | 15.0 | 2.9 |

The data presented in Table 1 demonstrate the high fruit yield potential of the new variety. Berries of 'Motueka' are suitable for consumption as fresh fruit and are very well suited for processing. The color of the processed product is a similar red to that of 'Marcy' and 'Skeena', the standard varieties for processing in New Zealand, although lighter than that of 'Meekeer' or 'Willamette', the standard varieties for processing in the United States.

BRIEF DESCRIPTION OF THE DRAWINGS

The accompanying photographs show typical specimens of the new variety in color as true as is reasonably possible. The photographs were prepared during 1999 and 2000 and depict three year-old plants and plant parts grown outdoors at HortResearch Nelson, New Zealand.

DETAILED DESCRIPTION

Figure 1:
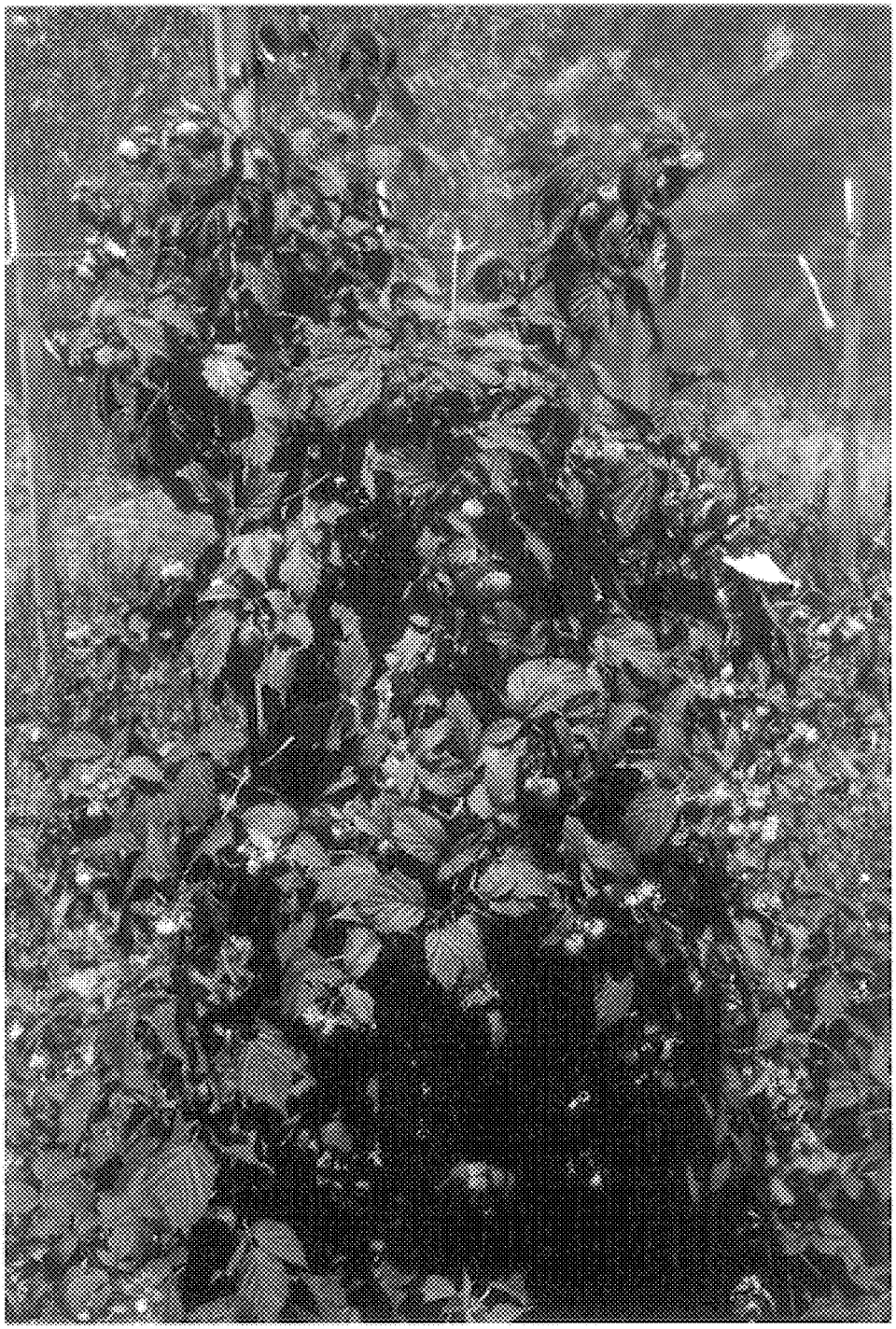
FIG. 1 illustrates a fruiting plant of the new variety showing the spineless growth and productive hanging fruiting laterals.

Horticultural terminology is used in accordance with UPOV guidelines for raspberry. All dimensions in millimeters, weights in grams (unless otherwise stated). Where a color reference is given, these refer to The R.H.S. Colour Chart, The Royal Horticultural Society, London, $4^{th}$ Edition, 2001.

The specimens described were three years old growing in the field at HortResearch Nelson. The plants were managed under practices to a standard considered reasonably acceptable in the horticultural industry. The observations were made in the 1999–2000 season. Environmental data for the growing area demonstrate conditions in spring and early summer (equating to the harvest period for the variety) as follows:

Spring (September/October); mean daily temperature in the range 10–12° C. (mean daily minimum 5.8° C., mean daily maximum 16.5° C.

Early summer (December/January); mean daily temperature 16.8° C. (mean daily minimum 11.1° C., mean daily maximum 22.4° C.

A cool temperate area, frost conditions are typically experienced in winter, with the lowest winter temperature unlikely to be colder than −10° C. Average annual rainfall is approximately 1125 mm.

Plant and foliage

Figure 3:
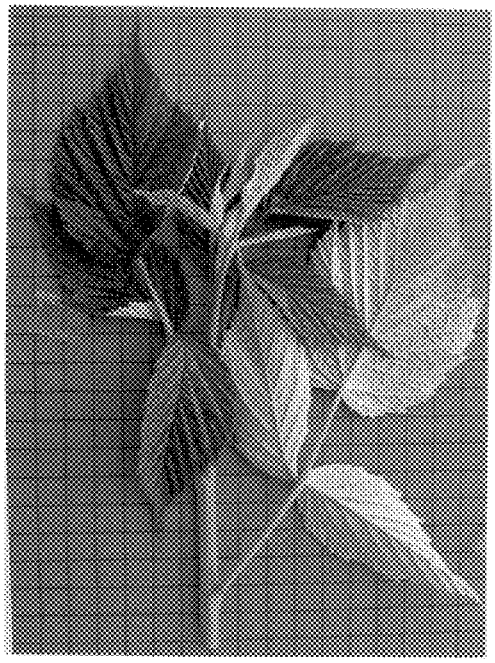
FIG. 3 illustrates the shoot tip of a primocane of the new variety with the leaflets at various stages of development.
Figure 4:
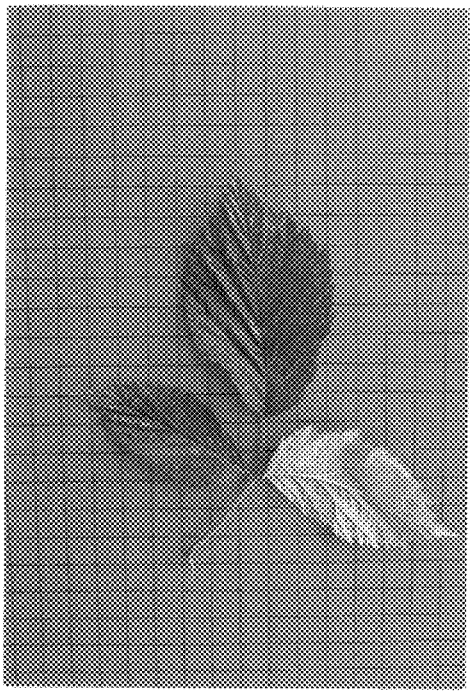
FIG. 4 illustrates fully opened leaflets of the new variety from a floricane showing the upper and lower surface of the leaves.
Figure 5:
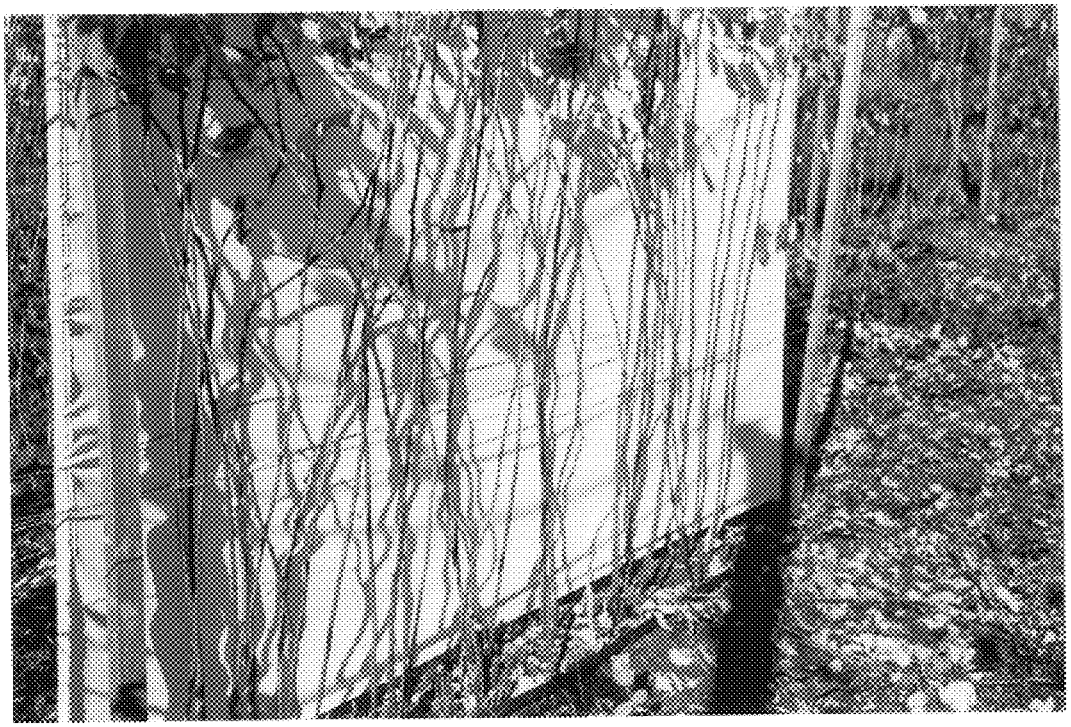
FIG. 5 illustrates the dormant canes of the new variety showing the light tan cane color and the complete absence of spines on the canes.

The plant exhibits a very upright growth habit (FIG. 5). Typical mature plant height is commonly in the range 1750 to 1950 mm, although may vary with the growing conditions. Moderate vigor is exhibited. Cane length is typically in the range 1600–1800 mm. Internode length is typically in the range 50–60 mm. Spines (prickles/thorns) are absent on new canes, and also on those developed in the previous season. The canes are upright with a leafy presentation, and are typically a light brown-tan coloration (near Greyed-orange 175A) during the winter. Some purple coloration (near Purple N77A) is also evident on the upper portion of the cane, the degree of coloration varying plant to plant. The fruit is borne primarily on the previous year's growth. The fruiting laterals are typically in a hanging attitude. The leafy coverage tends to provide hand pickers with poor fruit presentation at harvest time but the leafiness promotes effective harvest by machine. The leaves are compound, moderately crinkled, flat, and moderately glossy (FIGS. 3 and 4). The number of leaflets per internode is predominantly three. While the majority of leaflets are separate, they are occasionally fused. The base of the leaflet is cordate in shape and leaflets typically average 72 mm in diameter and 114 mm in length. The coloration of the upper surface of the leaf is green (near Green 137B), the underside being markedly lighter in coloration (near Greyed-green 191D). While the leaves do not have distinguishing marginal or vein coloration, the venation has noticeable rises and falls. The leaf petiole typically averages approximately 52 mm in length, and 1.6 mm in diameter. It is near Yellow-green 145A in color, with some Anthocyanin coloration observed (near Red-purple 60A). The plant is particularly distinguished by the presentation of the foliage—the petiole is at an angle of approximately 75° to the stem, however the blade of the leaf is presented at an angle of 90°–110° resulting in a distinctive downward presentation of the foliage. Young shoots are semi-erect and new shoots commonly show weak anthocyanin coloration.

Inflorescence

White flowers are borne on short slender pedicels that lack spines (thorns/prickles). The time of bloom is mid-season for a summer-fruiting raspberry. At HortResearch Nelson, the date bud burst commences is approximately September $2^{nd}$, with fifty percent of buds burst by mid September (approximately September $12^{th}$). Typically there are five petals elongated ovate in shape with a rounded apex and flat base. The petals average approximately 6.5 mm in length and 3.2 mm in width. They are typically smooth in texture, have a smooth margin and are near White 155C in color. The pedicel length averages approximately 22.0 mm (observed range approximately 20 to 30 mm). However, the more basal the pedicel the longer it commonly becomes with pedicel lengths up to about 50 mm being observed. The pedicel averages approximately 0.75 mm in diameter and is near Yellow-green 144B in color. A typical flower diameter is approximately 22 mm (from sepal tip to sepal tip i.e. the widest part of the flower). The flowers are predominantly borne singly, although sometimes in clusters of two or more. Terminal branch flower clusters frequently consist of two flowers and basal flower clusters may number three to five. The flowers have no discernible fragrance. Five sepals are present. These are green in coloration (near Yellow-green 144B) and measure approximately 5.5 mm in length from base to tip. The reproductive organs are typical for flowers of *Rubus idaeus* L.; the stigmas average approximately 6.5 mm in length and are near Green-white 157A in color; there are approximately 80–90 anthers, these being near White 155A in color; the filaments averaging approximately 4.5 mm in length and being near White 155C in color.

Harvest

At HortResearch Nelson, the typical start date for picking the new variety is December 8. Fifty 50 percent of the harvest is typically completed by December 27, and harvest ceases approximately January 28. The harvest period is commonly longer for 'Motueka' than for either 'Marcy' or 'Skeena'. Similarly, the date at which 50 percent of harvest is complete is approximately 10 days later for 'Motueka' than for 'Marcy' and 4 days later than that for 'Skeena'.

'Motueka' is well suited for harvest by machine. In trials with a Korvan 9000 harvester a high percentage of ripe fruit was removed and successive harvests were uniform and high quality. Few green fruit were removed, even at high beater frequencies and the amount of reject fruit to be removed from grading belts was minimal.

Fruit

Figure 2:
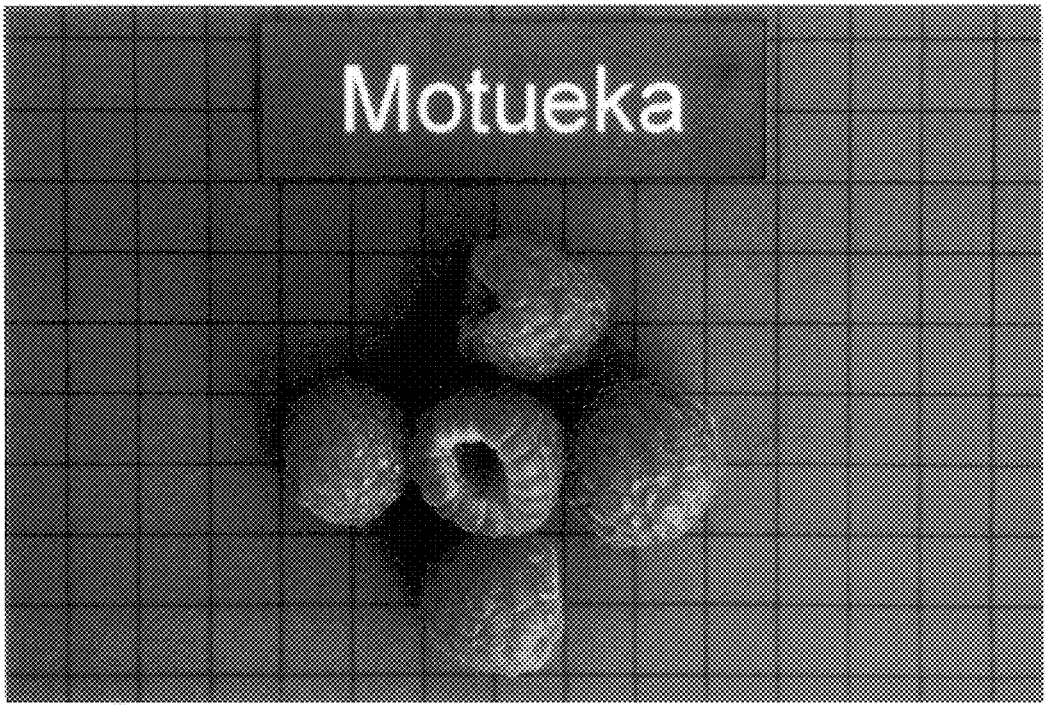
FIG. 2 illustrates enlarged close-up end and side views of typical fruit of the new variety.

The berries formed on 'Motueka' are medium-large in size and are typically longer than broad. The fruit is short conical in configuration (FIG. 2) and is bright in appearance with medium glossiness. The berries are medium-firm and fleshy, with good flavor. Berries generally weigh approximately 3.5 g, although larger fruit, up to 5 g, may be observed, and average approximately 21.0 mm in length and 18.0 mm in diameter. The fruit are medium red in color similar to the variety 'Malling Orion' (not patented) (external color near Red 53A, internal color near Red 46A). The seeds average approximately 2.7 mm in length and 0.8 mm in diameter, and are near Greyed-orange 165D in color when dry. Seed weight typically averages approximately 1.9 mg. Fruit of 'Motueka' are well suited for individually quick frozen storage and excellent for processing, producing a high flavored product.

Pest and disease resistance

Resistance to aphids is unknown. Since the selection of 'Motueka' in 1993 numerous tests for raspberry bushy dwarf virus (RBDV) have been done using ELISA but on no occasion has the virus been detected despite high infection pressure. From this we suggest that 'Motueka' is likely to be resistant to the common strain of RBDV found in New Zealand.

If 'Motueka' is grown in dense rows and conditions are favorable for the infection of gray mould (*Botrytis cinerea*) some problems with fruit rot may be encountered. The susceptibility to fruit rot has been observed to be less than that shown by 'Skeena' or 'Marcy'.

Cultivation

'Motueka' performs well in the cool temperate climate of the Nelson region under standard management practices for commercial raspberry production.

I claim:

1. A new and distinct variety of raspberry plant, *Rubus idaeus* L, substantially as herein shown and described.

* * * * *